US006555155B2

(12) United States Patent
Saxby et al.

(10) Patent No.: US 6,555,155 B2
(45) Date of Patent: *Apr. 29, 2003

(54) METHOD AND APPARATUS FOR HARVESTING, DIGESTION AND DEHYDRATING OF KRILL HYDROLYSATES AND CO-DRYING AND PROCESSING OF SUCH HYDROLYSATES

(75) Inventors: David J. Saxby, West Vancouver (CA); John A. Spence, West Vancouver (CA); Gregar Saxby, West Vancouver (CA); Pedro Aloise, Vancouver (CA)

(73) Assignee: Biozyme Systems, Inc., Vancouver (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/020,695

(22) Filed: Feb. 9, 1998

(65) Prior Publication Data

US 2002/0076468 A1 Jun. 20, 2002

Related U.S. Application Data

(63) Continuation-in-part of application No. 08/740,004, filed on Oct. 21, 1996, now Pat. No. 6,112,699.

(30) Foreign Application Priority Data

Feb. 7, 1997 (CA) ............................................... 2197137

(51) Int. Cl.[7] ............................................... A23L 1/326
(52) U.S. Cl. ..................... 426/643; 426/574; 435/68.1
(58) Field of Search ........................ 435/68.1; 426/56, 426/574, 643, 656, 384, 465, 469, 471, 652

(56) References Cited

U.S. PATENT DOCUMENTS

| 2,631,835 A | 3/1953 | Jones |
| 3,595,540 A | 7/1971 | Whitcombe |
| 3,662,474 A | 5/1972 | Huthwaite |
| 3,768,552 A | 10/1973 | Ciraud |
| 3,775,041 A | 11/1973 | Buttner |
| 3,859,734 A | 1/1975 | Wahlgren |
| 3,890,566 A | 6/1975 | Nordblad et al. |
| 4,036,993 A | * 7/1977 | Ikeda et al. .................. 426/7 |
| 4,041,181 A | 8/1977 | Burrows et al. |
| 4,347,670 A | 9/1982 | Wear et al. |
| 6,056,981 A | * 5/2000 | Saxby ..................... 426/471 |

FOREIGN PATENT DOCUMENTS

| EP | 467003 A1 | 1/1992 |
| GB | 1084005 | 1/1983 |
| GB | 2034492 | 12/1991 |
| JP | 05030923 | 2/1993 |
| WO | 82-02645 | 8/1982 |
| WO | WO 89/01031 | 2/1989 |
| WO | WO 89/10960 | 11/1989 |
| WO | WO 90/05026 | 5/1990 |

OTHER PUBLICATIONS

Paper entitled "A New Process for the Utilization of Antarctic Krill" by T. Ellingsen and V. Mohr, date N.A.
Paper entitled "Autolysis of Antarctic Krill Protein and Its Inactivation By Combined Effects of Temperature and pH*" by M. Kubota and K. Sakai, Tokyo University, Mar. 1978.
Journal Article, "Posibilidades de Elaboracion y Comercialization . . . ", Budzinski et al, 5 pages, (Spanish), Jan. 1986.

* cited by examiner

Primary Examiner—Keith Hendricks
(74) Attorney, Agent, or Firm—John Russell Uren

(57) ABSTRACT

Method and apparatus used in producing a feed product or premix and the products made by the method. A predetermined quantity of krill hydrolysate is added to a predetermined quantity of dry carrier with or without a predetermined quantity of liquid marine protein. The mixture is subject to evaporation and drying steps in which relatively heavier particles are separated from relatively lighter particles. The mixture may be blended, ground and subject to chemical reaction in a balance tank prior to entering a dryer. The dryer utilizes a warm air source, a tower and a cyclone to dry the mixture following its entry into the dryer. Temperature sensitive enzymes or other bioactive products may be added to the product produced from the dryer. A method for obtaining enzymes from a fresh krill extract or an autolyzed krill preparation and the product are also disclosed. A method for separating the bound protein and pigments from crustacean waste using krill enzymnes and a product produced by the method are also described.

28 Claims, 12 Drawing Sheets

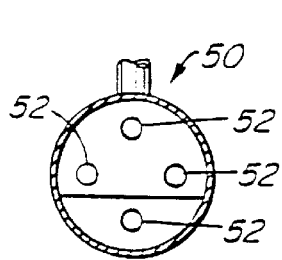
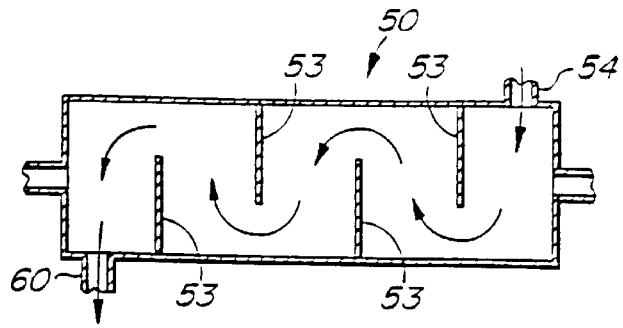
FIG. 4A   FIG. 4B
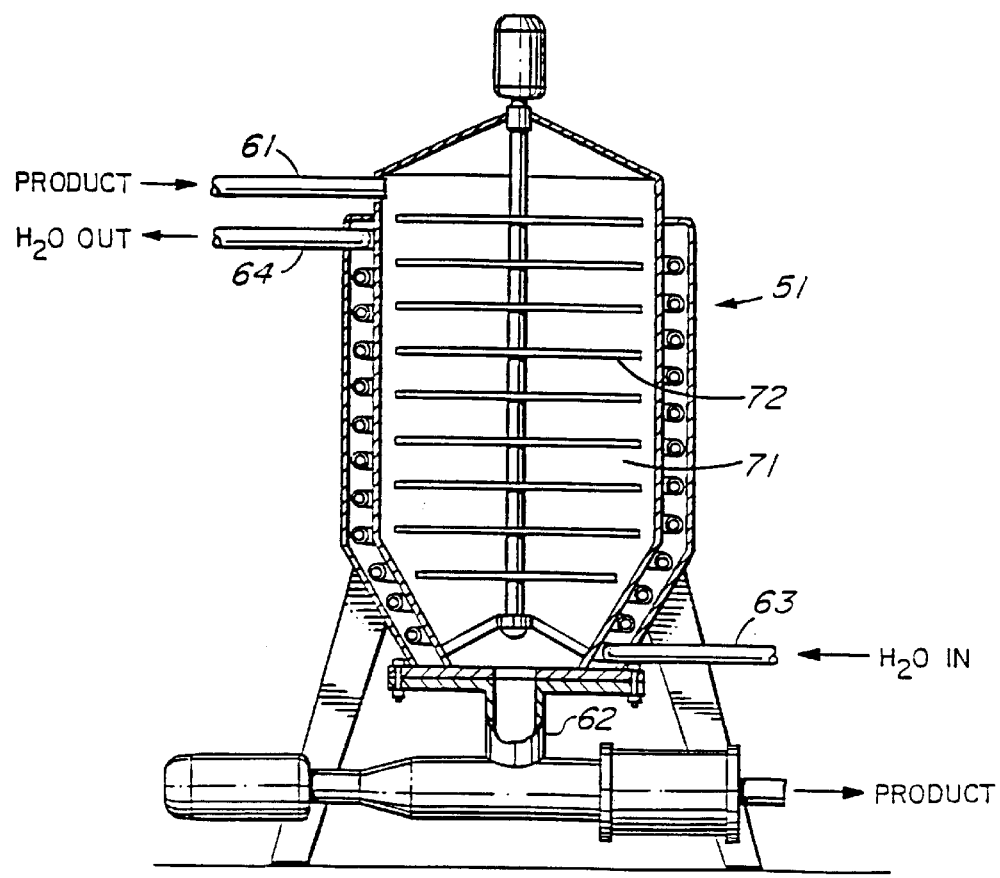
FIG. 5

METHOD AND APPARATUS FOR HARVESTING, DIGESTION AND DEHYDRATING OF KRILL HYDROLYSATES AND CO-DRYING AND PROCESSING OF SUCH HYDROLYSATES

This application is a continuation-in-part of Ser. No. 08/740,004, filed Oct. 21, 1996, now U.S. Pat. No. 6,112,699.

INTRODUCTION

This invention relates to a method and apparatus used in producing a feed product or premix and the product made by the method and, more particularly, to a process using co-drying to dry a mixture of krill hydrolysate and dry carrier or a mixture of krill hydrolysate, fish hydrolysate and dry carrier. The invention further relates to recovering enzymes from krill and, more particularly, to recovering enzymes from both freshly harvested and hydrolyzed krill. The invention further relates to utilising krill enzymes for removing protein from marine and biological wastes and, more particularly, for removing protein, chitin and other constitutents from crustacean and other marine wastes.

BACKGROUND OF THE INVENTION

With the advent of increasing activity in aquaculture or fish farming in the early to mid-1980s, research has been ongoing into increasing productivity or growth rate and reducing the mortality rate of fish raised in aquaculture conditions since survival of such fish is important. One such factor relates to enhancing the nutritional value and palatability of feed used in raising such fish. In addition to the nutritional value, it is desirable to reduce the cost of feed to such fish since, typically, the feed totals approximately 40 to 50% of the cost of raising the fish. Such feed should be a high quality feed to meet the objectives of having high nutritional value to maximize growth and to reduce fish mortality.

The requirement for feed products in aquaculture is projected to grow substantially and, as a result, there is and will be pressure to obtain the necessary ingredients for fish food. The possibility of using zooplankton and, in particular, euphausiids, as a fish feed, appetizer or food product has been investigated and has been found to be possible and desirable, particularly as a feed product.

In addition, blends of krill hydrolysates and fish hydrolysates or any one of these with a dry carrier, can provide alternatives to fish meals in aquaculture and other animal feed diets. Euphausiids are a natural feed harvested directly from coastal waters and have a high nutritional value but, previously, the cost of harvesting and processing such zooplankton for a feed product has been prohibitively expensive.

As well, the questions of the availability of the biomass of such zooplankton and its harvesting, handling, storage and processing are parameters that must be investigated in order to determine whether the product would be appropriate as a feed product.

Through papers written by Fulton and other authors, the use of zooplankton as a food or feed product has been contemplated for some time. In particular, antarctic krill (*Euphausia superba*) for human consumption have been investigated, although relatively little work has been investigated related to aquaculture. The use of *Euphausia pacifica* in the coastal waters of British Columbia, Canada has been considered in relation to its use in aquaculture and other animal feeds.

It appears, from those investigations, that the necessary biomass is available in coastal waters. Previously, euphausiids have been used as a pet food ingredient and some aquaculture operators have used euphausiids as a feed product. The euphausiids were used for such purposes in a frozen form after being harvested and in some cases, the euphausiids were freeze dried following harvesting. This is an expensive procedure.

In processing feed products, it has typically been the case that the ingredients used in such feed products are heated to a high temperature around 100° C. when the product is processed and dried. By heating the product to such a high temperature, it is believed that the enzymes and other proteins in the product are denatured. If, however, it is intended to utilize the product for early stage or juvenile aquaculture, which young fish have relatively undeveloped digestive systems, it is desirable that in some application, the euphausiid products maintain a certain proportion of enzymes which will assist the digestive process in juvenile and other life stages. If the theory that enzymes are advantageous in nutrition is correct, such destruction of the enzymes during the aforementioned drying process is disadvantageous.

It is also desirable to have a natural product, where the proteins are not denatured, available for early stage juvenile or larvae feed. In some previous products, exogenous enzymes have been added to the zooplankton mix. However, the addition of such enzymes is difficult to control and can result in a complete hydrolysis of the proteins to amino acids. The presence of free amino acids in the feed needs to be controlled since they can create an inferior product of substantially reduced value as a feed product.

It has been shown, surprisingly, that the degree of enzyme activity which results in determining the digestibility of a product, reaches a relatively constant value after a certain period of time in a natural product. Recent investigations conducted by the applicant have confirmed this characteristic for *Euphausia pacifica*. This characteristic was first discovered in relation to *Euphausia superba* by Kubota and Sakai in a report entitled "Autolysis of Antarctic Krill Protein and Its Inactivation by Combined Effects of Temperature and pH", Transactions of the Tokyo University of Fisheries, number 2, page 53–63, March 1978. However, the antarctic krill study done by Messrs. Kubota and Sakai had the objective of limiting enzyme activity which was deleterious to obtaining a food as opposed to a feed product. Messrs. Kubota and Sakai wished to inhibit the enzymatic activity by certain processing techniques which they considered desirable when the product was intended as a food product.

An appropriate degree of hydrolysis is obtained during the digestion of the euphausiids. The approximate degree of hydrolysis will vary depending on the final application and it can be monitored by measuring the apparent viscosity in the final product. Further processing may then take place in order to make a useful product for commercial feed. Such processes may include adding acid to obtain an acid stabilized product concentrating fractionating or drying the product. A variety of drying techniques such as freeze drying, spray drying, or vacuum and air drying. Spray drying, as well as some other drying processes, however, are done at temperatures that will permanently inactivate the enzymes in the euphausiids which, as earlier mentioned, may be undesirable for aquaculture purposes although it is acceptable for purposes where the product is intended to be used as a carotenoid biopigment for coloring purposes in both feed and food products or as a source of protein, fatty acids, minerals or other nutrients.

SUMMARY OF THE INVENTION

According to one aspect of the invention, there is provided a method of producing a feed product comprising the steps of adding a predetermined quantity of krill hydrolysate to a quantity of dry carrier to produce a mixture and co-drying said mixture to obtain an end product. The dry carrier may conveniently be a plant protein, dry krill, fish meal, byproduct meal or other dry ingredient suitable for inclusion in a diet.

According to a further aspect of the invention, there is provided a product produced by adding a predetermined quantity of krill hydrolysate to a quantity of liquid marine protein and a quantity of dry carrier to produce a mixture and co-drying said mixture.

According to a further aspect of the invention, there is provided a co-drying apparatus for drying a mixture of krill hydrolysate with or without an evaporator and liquid marine product and a dry carrier comprising a dryer for concentrating, mixing, agitating, heating and separating particles of said mixture.

According to still a further aspect of the invention, there is provided a method of obtaining an enzyme extract from a liquid krill hydrolysate comprising the steps of subjecting said hydrolysate to decanting and then to centrifugation to obtain a clarified liquid and further subjecting said clarified liquid to ultrafiltration using a membrane with a capacity to retain said enzymes having a molecular weight greater than 10,000 daltons and the product produced by the method.

According to still a further aspect of the invention, there is provided a method of obtaining an enzyme extract from fresh krill comprising the steps of squeezing said krill to obtain an aqueous extract and subjecting said aqueous extract to ultrafiltration with a membrane adapted to retain enzymes having molecular weights above 10,000 daltons and the product produced by the method.

According to still yet a further aspect of the invention, there is provided a method for removal of protein from non-stabilized or fresh crustacean shell wastes comprising grinding said crustacean wastes and water, transferring said product to a digester, adding a predetermined quantity of krill enzymes to said digester, subjecting said mixture to digestion for a predetermined time period at a predetermined temperature, dewatering said digested product to obtain a first portion being relatively enzymatically active and relatively high in protein and a second portion of shell material relatively high in chitin and low in protein.

According to still yet a further aspect of the invention, there is provided a method for removal of protein from acid stabilized shell wastes comprising grinding said crustacean wastes, transferring said small particulate size shell wastes to a digester, adding a predetermined quantity of krill enzymes to said digester, subjecting said mixture to digestion for a predetermined time period at a predetermined temperature, dewatering said digested product to obtain a first portion being relatively enzymatically active and relatively high in protein and a second portion of shell material relatively high in chitin and low in protein.

BRIEF DESCRIPTION OF THE SEVERAL VIEWS OF THE DRAWINGS

Specific embodiments of the invention will now be described, by way of example only, with the use of drawings in which:

FIGS. 4A and 4B are end and side sectional views of the heat exchanger used to raise the temperature of the harvested euphausiids prior to the digester process;

FIG. 5 is a diagrammatic side sectional view of the digester used to create the desired enzyme activity within the euphausiids;

DESCRIPTION OF SPECIFIC EMBODIMENT

Figure 1A:
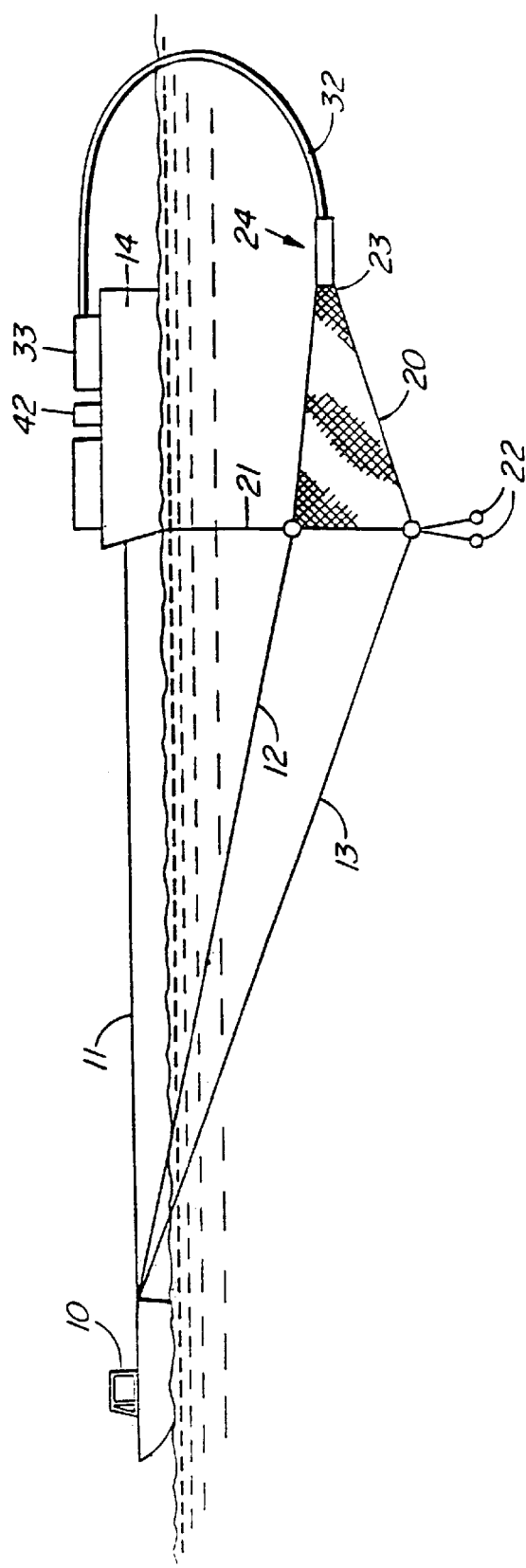
FIG. 1A is a diagrammatic isometric view of a fishing vessel with an attached net which utilizes the euphausiid harvesting technique according to the invention.

Referring now to the drawings, a towing vessel 10 is illustrated in FIG. 1. A plurality of towing ropes 11, 12, 13 are connected to the towing vessel 10 in order to tow a barge 14 and a net 20. A plurality of ropes 21 (only one of which is shown) are connected to the net 20 and extend downwardly from the barge 14. Weights 22 are connected to the bottom of the open forward facing portion of the net 20 in order to maintain the net 20 at a desired and predetermined depth where the concentration of zooplankton is satisfactory.

Figure 2A:
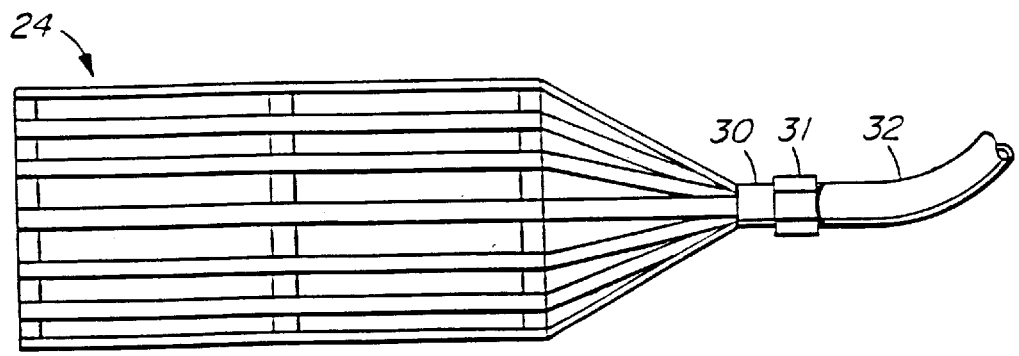
FIG. 2A is a diagrammatic side view of a cage which is used to maintain the cod end of the fishing net illustrated in FIG. 1 in an open position and which is further used to transport the harvested euphausiids to the harvesting vessel.

The cod or rearward end 23 of the net 20 is maintained in an open condition by the use of a cage generally illustrated at 24 in FIG. 2. Cage 24 is of cylindrical configuration and is positioned within the cod end of net 20. It is made from aluminum and is preferably corrosion resistant. A fitting 30 is welded to the downstream end of the cage 24 and one end of a swivel connection 31 is joined to the fitting 30 to prevent fouling the net in the event components become unstable under adverse harvesting conditions. A hose 32 is connected to the other end of the connection 31.

Referring again to FIG. 1, hose 32 extends upwardly from the cod end of the net 20 to the barge 14. A pump of a variety of configurations but, conveniently, a diaphragm sump pump 33, is located at the other end of the hose 32 on barge 14. A dewatering trough is generally shown at 34 and is illustrated in FIGS. 2B and 2C. Dewatering trough 34 has a lengthwise generally rectangular configuration and is also located on barge 14. Dewatering trough conveniently takes the configuration of a "lazy L". A set of screens 40 positioned at obtuse angles are utilised to allow water to drain from the pumped euphausiids and exit the trough 34 through drain pipes 41 while the euphausiids accumulate within the dewatering trough 34.

A blast freezer 42 was also located on the barge 14 to stabilize the harvested euphausiids. The blast freezer 42 subjects the euphausiids to a temperature of approximately +90 to −17° C. and is used to freeze the dewatered euphausiids and stabilize the product for further processing. The euphausiids accumulate within the dewatering trough 34 and which are periodically removed from the trough 34 from time to time for freezing. Thereafter, the frozen euphausiids are transported to a processing location and processed as described hereafter. Alternatively, the euphausiids may conveniently be processed aboard a vessel.

In prototype demonstrations, the net 20 utilised for the harvesting operation was a specially designed 13 ft. by 21 ft. plankton net suspended from a 46 ft. aluminum barge. The pumping action was by a three inch diaphragm pump located on the barge 14 and the freezing action occurred within a minus seventeen (−17° C.) degree centigrade blast freezer 42.

Figure 3:
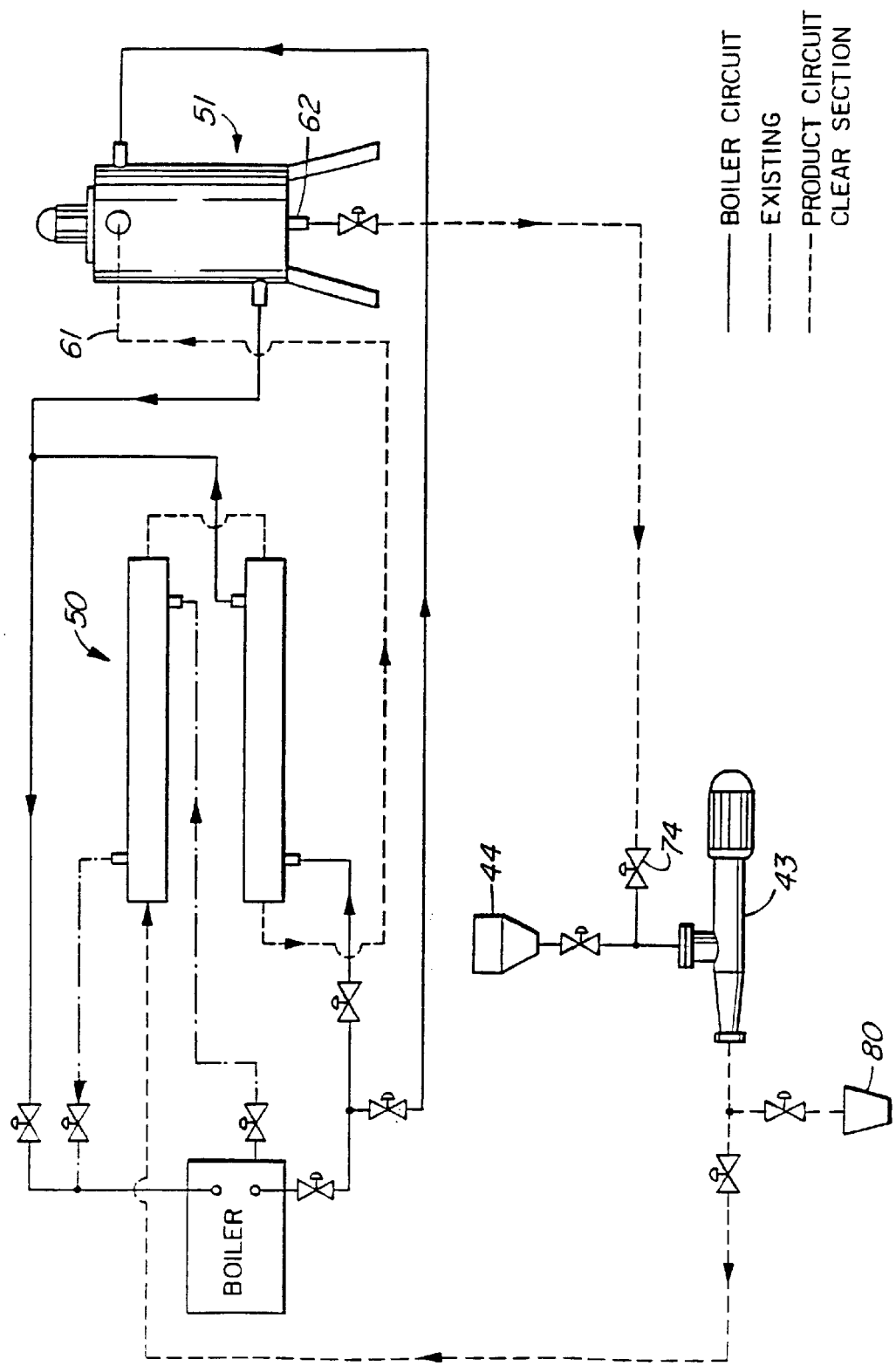
FIG. 3 is a diagrammatic process chart illustrating the processing of the euphausiids subsequent to the dewatering steps illustrated in FIG. 2 and prior to the drying step.

As earlier described, the frozen euphausiids are transported to a processing location in order to transform the euphausiids into the desired feed product. Reference is now made to the flow chart of FIG. 3.

A pump 43 is connected to a hopper 44 which receives the euphausiids which are now in a thawed condition. Pump 43 is connected to a heat exchanger generally illustrated at 50 and diagrammatically illustrated in FIG. 3. The heat exchanger 50 is intended to raise the temperature of the euphausiids to a temperature of approximately 40° C. to 60° C. which will more closely approximate the temperature maintained in the digester which is generally lower than 70° C. and which digester is generally illustrated at 51. Digester 51 is located downstream of the heat exchanger 50 in the process illustrated in FIG. 3.

Although several different types of heat exchangers may be used, heat exchanger 50 conveniently comprises a plurality of pipes 52 (FIG. 4A) in which the euphausiids are conveyed through the heat exchanger. Heated water enters the inlet 54 of the heat exchanger 50 and is circulated through the heat exchanger 50 generally following the flow path seen in FIG. 4B which utilizes a plurality of baffles 53. The heated water exits the heat exchanger at outlet 61. Following the increase of temperature created in the euphausiids by the heat exchanger 50, the euphausiids pass to the digester 51.

Digester 51 is seen is greater detail in FIG. 5. It comprises a product inlet 61 and a product outlet 62. A water inlet 63 and a water outlet 64 are provided. A water jacket 70 through which the heated water circulates surrounds the cylindrical cavity area 71 of the digester 51 which contains the euphausiids. A plurality of stirring discs 72 are located vertically within the cavity area 71 of the digester 51 and are used to stir the euphausiids when they are positioned within the digester 51. A valve 73 is used to close the product outlet 62 so as to maintain the euphausiids within the digester 51 until the proper temperature and time for the desired enzyme action within the euphausiids has taken place. The time period has conveniently extended between thirty (30) minutes and two (2) hours.

It is thought that a degree of hydrolysis will enhance digestibility of the feed product particularly for early stage larvae or juveniles but also for virtually all fish. This degree of hydrolysis is determined by the applications and will be monitored by measuring the apparent viscosity in the final product. In utilising the digester 51 illustrated in FIG. 5, a batch process is currently being used with a volume of euphausiids of 250 lb./hr being used.

Figure 6:
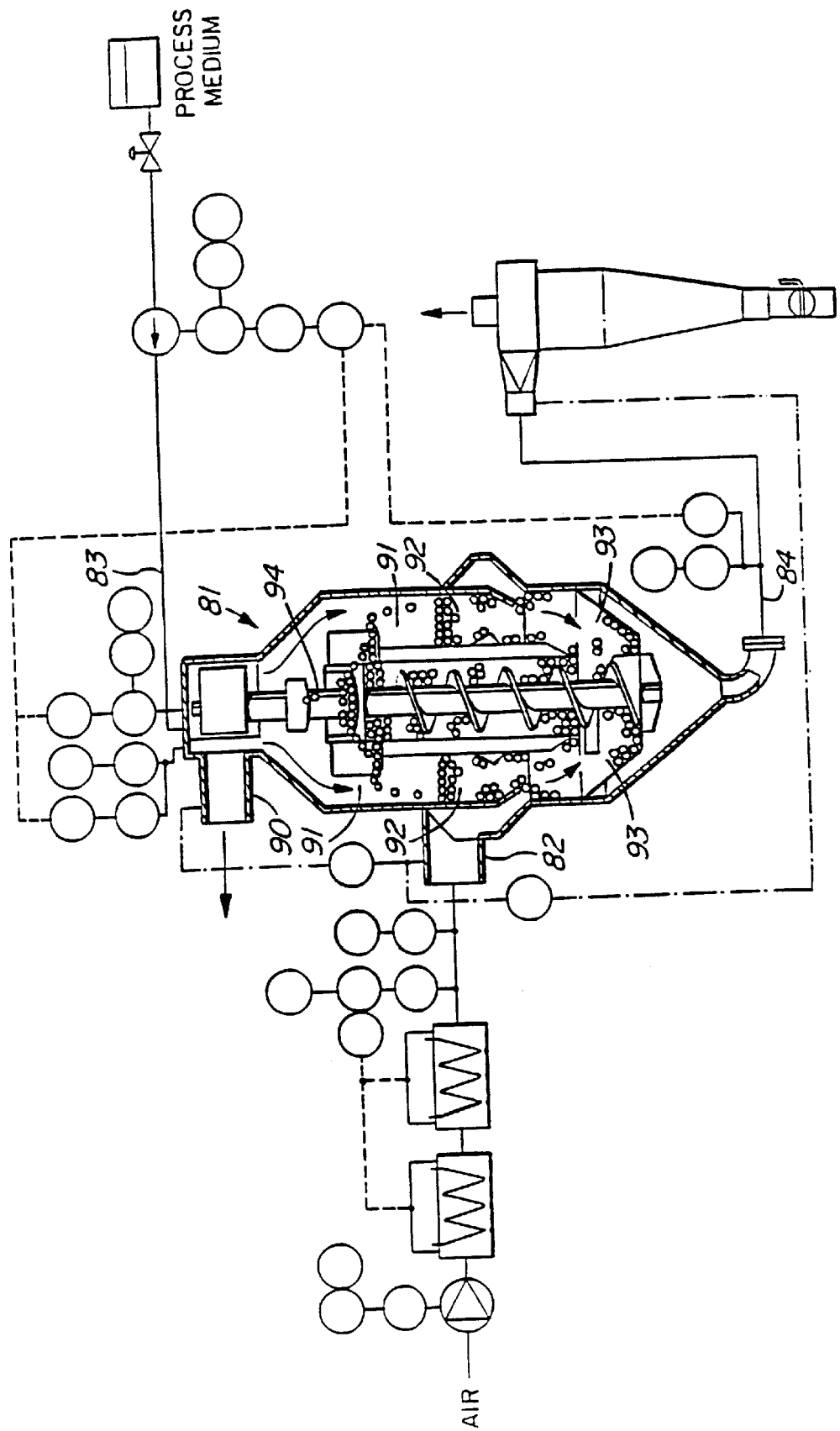
FIG. 6 is a diagrammatic side sectional view of a ball drier used to dry the euphausiids following removal of the euphausiids from the surge tank located downstream from the digester.

The valve 62 is then opened and the quantity of euphausiids within the digester 51 pass through the valve 62 and are transported through valve 74 to the surge tank or heated batch storage vessel 80 where they await treatment in the dryer, conveniently a ball dryer generally illustrated at 81 (FIG. 6) where relatively low and controlled temperatures can be applied to the euphausiids such that any enzymes existing within the euphausiids are not inactivated as would otherwise be the case in a normal drying process.

The euphausiids pass from the storage vessel 80 to the ball dryer 81 through product inlet 83 and, thence, about the periphery of the dryer 81 initially through the application zones 91 where the balls initially contact the euphausiids and begin the drying process. The ball dryer 81 performs a "soft" drying process which reduces damage to the euphausiids because of its gentle action by way of controlled temperature. The ball drying process utilises a continuous feed into the ball dryer 81 and a product flow of 15 lb./hr. is available.

As the balls and euphausiids move downwardly through the drying zones 92, they meet a counter-current flow of controlled-temperature drying air at less than 50° C. which air enters the ball dryer 81 through air inlet 82. Air flow, temperature and dwell time are precisely controlled and monitored within this zone. All of these are variable factors which depend upon whether the product is wet or dried and what period of time the product is intended to stay in the dryer 81.

In the separation zone 93 at the bottom of the dryer 81, the ball and euphausiids meet a co-current flow of controlled temperature air for final drying and separation. The dried euphausiids leave the ball dryer 81 through the product outlet 84 and pass to the packaging step. The drying balls are elevated by rotating helix 94 and recycled to the application zone 91 and the process continues.

One of many commercial and known dryers may be used for the air drying of the euphausiids.

It is contemplated that although the processing of the euphausiids has been described as taking place at a land location, such processing steps may take place at the harvesting location on board either the harvesting vessel or another vessel conveniently located nearby. This results in advantages in that the euphausiids need not be frozen following harvesting and need not be transported to a land based processing plant thereby resulting in considerable cost savings and quality improvement. In addition, the euphausiids may be introduced directly to a low temperature dryer on board a vessel following harvesting or to an evaporator. The dried or concentrated euphausiids, after being subjected to the digester and/or the drying processes, may then be stored on the vessel until a substantial quantity of krill hydrolysate concentrate has been obtained at which time they may be transferred to another vessel for transport to the processing vessel itself which, when full, will transport the euphausiids to the shore.

Likewise and while it is desirable for the digester and drying steps to take place concurrently and sequentially in the event the euphausiids are intended to be used as a feed product for juvenile and early stage larvae.

Figure 1B:
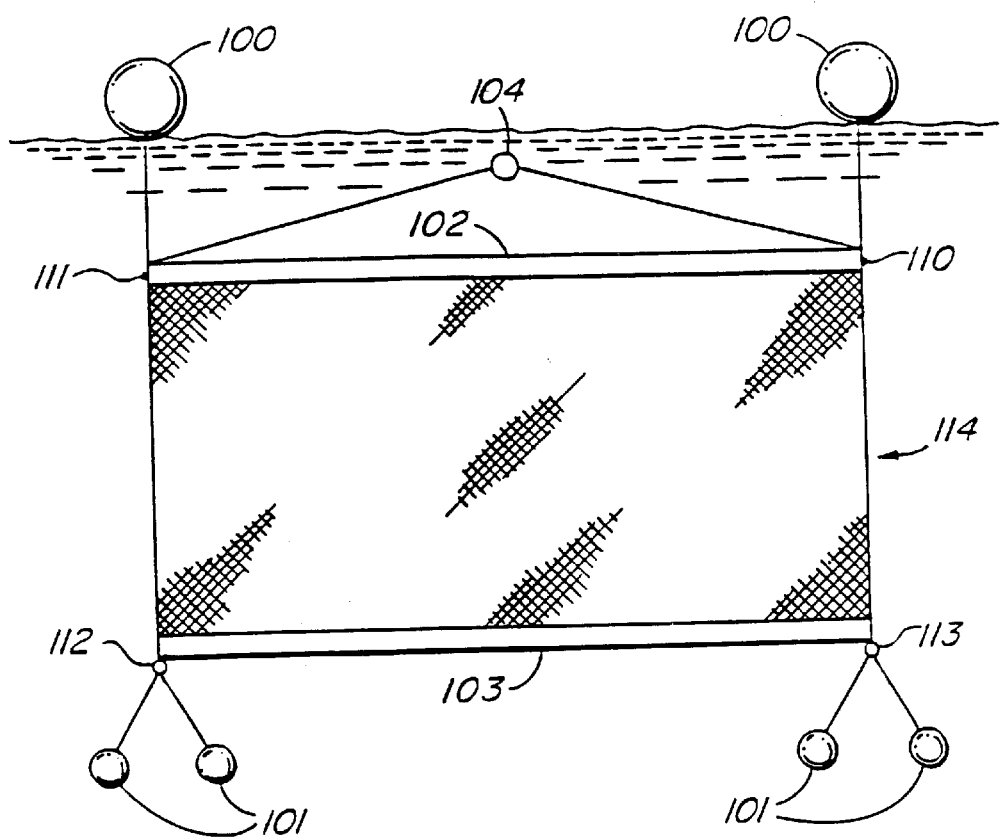
FIG. 1B is a diagrammatic front view of a net in an alternative harvesting technique according to the invention.
Figure 2B:
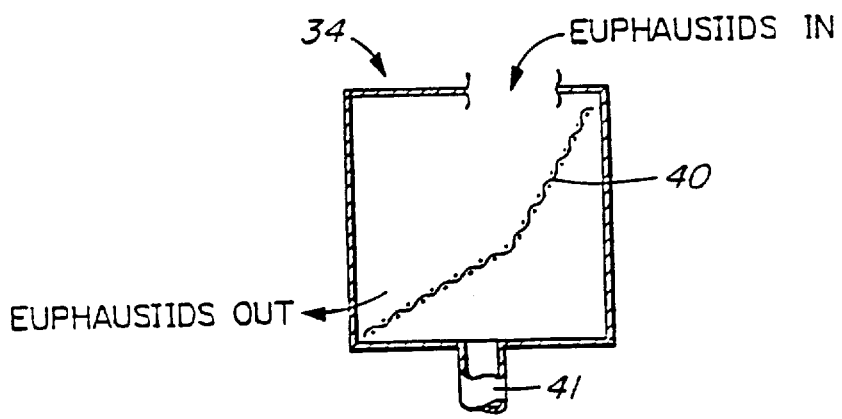
FIGS. 2B and 2C are side and rear views, respectively, of the dewatering trough used to remove water from the harvested euphausiids.
Figure 2C:
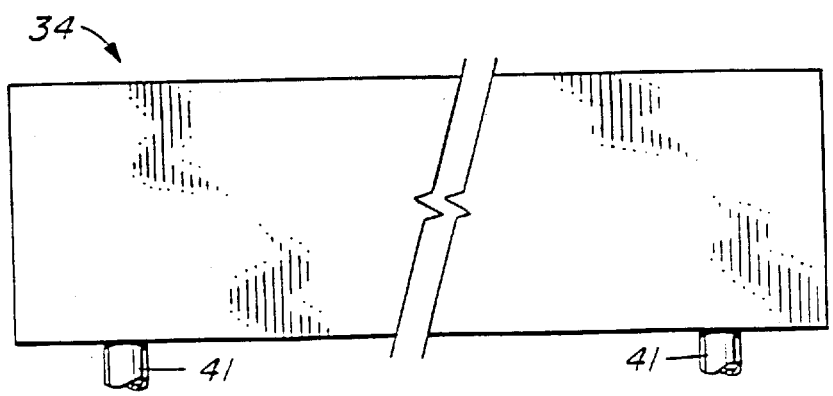

A further harvesting technique is contemplated in FIG. 1B. In this technique, weights 101 are connected to the mouth end of the net generally illustrated at 114 at the ends of the lower horizontal beam 103. Floats 100 are connected to the top horizontal beam 102 of the mouth end of the net 114. Depending on the size of the net 114, lines are connected on one end to attachment points 104, in the first instance or, alternatively, to points 110, 111, 112, 113 and, on the other end, to the towing vessel. The net 114 is pulled through the water gathering the zooplankton which enter the net 114 through the mouth.

Many applications for the hydrolysed krill and hydrolysed krill concentrate products are also contemplated because of the desirable characteristics of the of the krill hydrolysate in which the proteins and nutritional value is retained and improved through the partial digestions of the proteins. For example, fish under stress, which is common with cultivated species raised with aquacultural techniques, are reluctant to eat and, accordingly, therapeutic drug delivery and special diets used for such marine species are difficult to use because the fish do not find such products palatable. The hydrolysed krill products and other zooplankton products according to the invention may be used with such special diets and drug delivery by creating an enhanced flavour and enhanced assimilation when the medicinal product such as a pellet is coated or mixed with the hydrolysed zooplankton product in a liquid or paste form. Likewise, while other such products may include specially added amino acids and other compounds to enhance the flavour of the product, the hydrolysed krill according to the present invention preserves, enhances and optimises the level of certain free amino acids and other flavourants thereby allowing flavour enhancement with a natural product and without the addition of amino acids or other flavourants. Likewise, the krill hydrolysates retain the protein and nutrient quality including the original pigments, fatty acids, other nutrients and mineral elements. The activity of the enzymes, which are contained in the krill, is also retained in the hydrolysed natural product according to the invention. Such enzymes allow for enhanced digestion of feed by certain cultivated marine species by increasing the availability of peptides and free amino acids without creating additional harmful stress on such species.

Yet a further application contemplated by the present invention is the use of hydrolysed krill that is blended and codried in association with plant or vegetable protein and other dry carriers such as soymeal, corn gluten meal and canola meal in fish feed mixtures. The range of co-drying cariers used in the blending process include a wide range of dry animal or vegetable protein and feed ingredients including soy canola and other soil seed meals, coarse ground cereal gains and flours, oil seed concentrates and isolates, corn and cereal glutens, pea and pulse meals, oil seed and cereal processing by products and brans, dried yeasts, algae and other single cell organisms, milk powders, blood meal and other body fluid products, animal and poultry by products, fish and shellfish meals, and vitaminised mineral premixes. Such applications would increase the palatability, amino acid balance and other nutrient levels in the dry blended meal so that it can be used to replace fish meal in aquaculture feeds and other applications. Further enzymes in the hydrolysed krill products according to the invention are preserved following the hydrolysis and can be allowed to act on the plant proteins. The enhanced digestibility of a product combination of plant protein and hydrolysed krill is also contemplated to improve the efficiency of the feed and decrease the fecal load in the environment by fish fed with diets containing such combination. This can be an important feature with the rearing of cultivated marine and freshwater species. Likewise, the palatability of such non-fish meal proteins, in particular, plant proteins such as canola, corn gluten or soy meal is enhanced.

Experiments conducted to date utilize the enzymes in krill to carry out a limited hydrolysis of soy, canola and other plant proteins. For example, one part of dry canola or soy meal which has added ten percent (10%) wheat bran is blended with five (5) parts of hydrolysed krill. The hydrolysate is pumped from the digester to the feed stock hopper and the dry blend is added. The mixture is brought to the desired temperature while agitated in the digester for approximately one (1) hour. Measurements of phytic acid and the levels of the amino acids and ammonia are then taken. For example, 250 lbs. of krill is hydrolysed by bringing the krill to approximately 45° Celsius. The temperature is held for one (1) hour and is then blended with 5 lbs. of wheat bran with 45 lbs. of canola concentrate. The use of wheat bran is necessary to provide phytase, an enzyme which is absent in canola meal and krill. The phytic acid is dephosphorylated by phytase from the wheat bran. The phytic acid is acted on by the phytase enzyme. It is noted that the blend may be retained in the digester for an extended period, up to a period of four (4) hours or even longer.

In yet a further embodiment of the invention, it is contemplated that the wet krill hydrolysate product is evaporated and then mixed with and co-dried with other wet and dry products. Various predetermined ratios of wet krill hydrolysate and liquid marine products may be concentrated and then mixed with dry carrier conveniently in the form of dried krill products, dried vegetable protein and/or dried fish product, used in combination or singly. The resulting moist blend is subject to concentration, processing and co-drying in a dehydrator such as a dryer. A dehydrator system with the following characteristics has been found to work well, namely a type of flash and fluidized drier or combination thereof with an agitator and vertical or tangential flow of heated air. Although the temperature of the inflowing air may be high at impact (the impact temperature), the temperature of the product is not significantly increased in the dryer. This is an important element in the drying system. Following hot air impact and agitation, the water evaporates rapidly and the duration of the drying process is greatly reduced as set out in greater detail hereafter.

Co-drying the mixture of the krill hydrolysate, liquid marine product and the dry carrier product mixture has been found to be relatively economical at relatively low temperatures. Under such conditions, the krill proteins, pigments and other constitutents are substantially preserved. Thus produced, the product has unique benefits for dietary uses in aquaculture and animal feeds. These blended and agglomerated dry products are uniquely different from other product mixes. The unique sequences and control of the process provides initial agglomeration and adsorption of the krill hydrolysate with the dry carrier. It also preserves the unique nutrient quality of the krill hydrolysate in the blend without significant losses due to excess heat or oxidation during the drying process. Further, cost savings and economic advantages in the manufacture of the product are improved.

Depending on the moisture content of the dry carrier, liquid marine protein, and the krill hydrolysate, and the proportion of each in the mixture to be co-dried, the removal of moisture can be accomplished by a drying process at relatively low temperatures thereby to preserve the temperature and oxidation sensitive constituents including the krill constitutents and the krill pigments. Particles of the dry carrier are coated with, adsorbed and absorbed with the wet hydrolysate thereby facilitating the drying process by exposing a greater surface area of wet hydrolysate and/or liquid fish product for heated air to act upon. The mixture may then be fractured into smaller particles which further increases the available surface area to expedite the drying process. At the outset, the mixture may be placed in a reactor cell balance tank to permit chemical interactions between components of the mixture, such reactions including enzymatic activity of a wide range of enzymes including proteolytic, lipolytic and carbohydrate splitting enzyme prior to drying. A well-mixed, homogeneous mixture is prepared to reduce and to eliminate high moisture pockets. Water is then removed from this mixture by an evaporator and a subsequent dehydrator such as is described above and the endproduct is a dried krill premix or feedstuff blended with the aforementioned carrier. Temperature sensitive enzymes, flavorants or other bioactive products may be added to the cooled endproduct after the drying step. Alternatively, the krill hydrolysate may be combined with wet fish products and other carriers such as dry fish meal, corn meal, canola meal, oil seed meal, or other vegetable meals, used in combination or taken singly.

Figure 7:
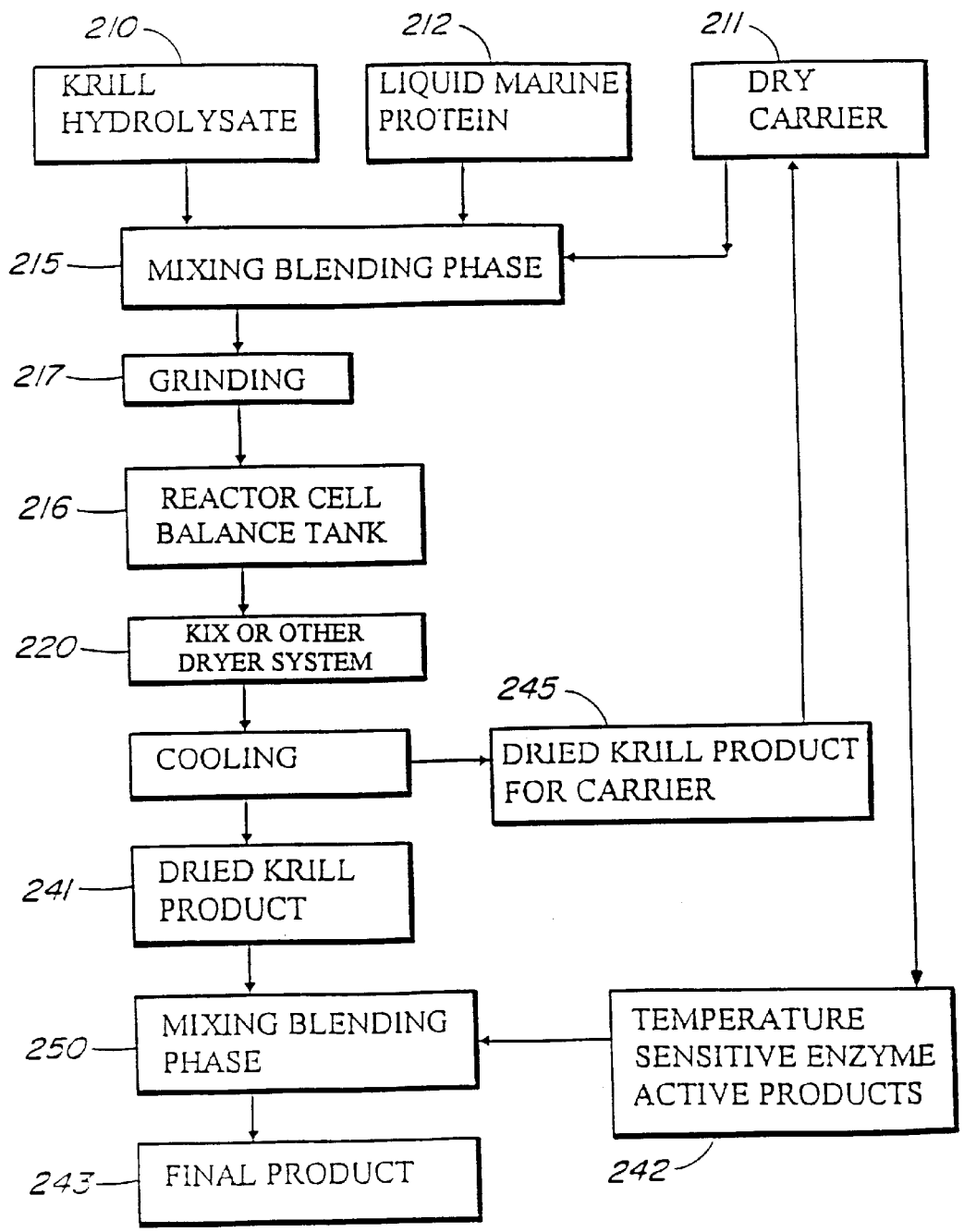
FIG. 7 is a flow chart illustrating the process of co-drying the product according to the invention.

Referring now to the drawings, FIG. 7 illustrates the steps of the co-drying process in its entirety according to the present invention. A predetermined quantity of wet krill hydrolysate product 210 is mixed with a predetermined quantity of liquid marine protein 212 and a predetermined amount of dry carrier 211, conveniently dried krill product, dried fish product and/or dried vegetable protein used in combination or taken singly. The resulting mixture is placed in a mixing blender 215, where the various ratios of hydrolysate, marine protein and dry carrier are thoroughly blended. The blending required will vary with the constitution of the mixture. The blended mixture is then ground within a grinder 217 where the mixture is reduced to particles of substantially uniform size. The ground mixture is then transferred to reactor cell balance tank 216 where the continuously stirred blended mixture is allowed to chemically react and/or undergo enzymatic action prior to the drying process. After the intended reaction has taken place in the tank 216, the mixture is conveyed to the dehydrator 220 for drying.

Figure 8:
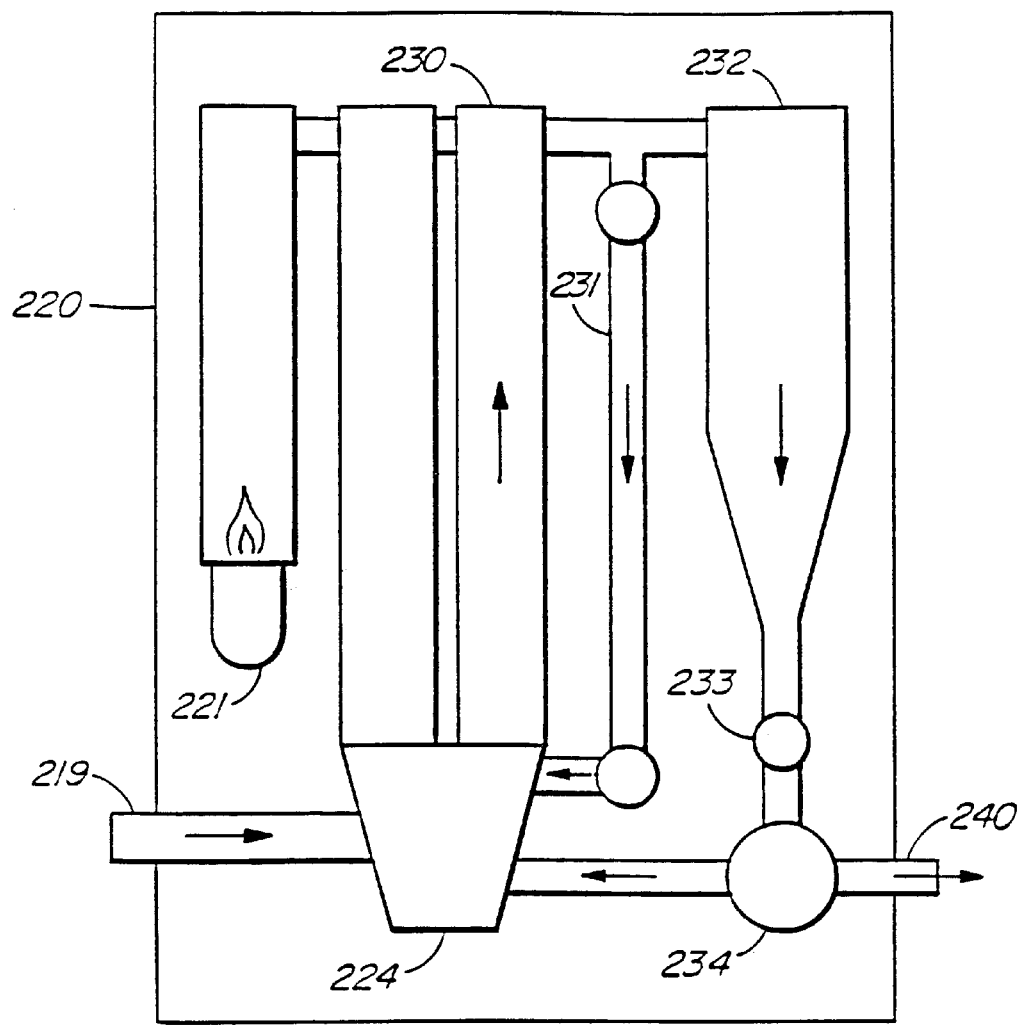
FIG. 8 is a diagrammatic view of the dehydrator used in the co-drying process according to the invention.

The dehydrator 220 is illustrated in greater detail in FIG. 8 and with reference thereto, the mixture enters the agitator bowl 224 of the dehydrator 220 through inlet 219 where the mixture is agitated into smaller particles which is intended to prevent clumping of the mixture. A continuous feed of mixture into the dehydrator 220 is intended through inlet 219.

Directly heated air from the burner 221 or indirectly heated air is directed to the agitator bowl 224 of the dehydrator 220 by way of fans (not illustrated) where the air mixes with particles of the mixture in the bowl 224. The particles are carried up the drying tower 230 by the column of hot air. The classifier 231 sorts the particles at the top of tower 230. Drier mixture consists of lighter, individual particles which proceed along the column of hot air into a cyclone 232. The classifier 231 redirects larger and heavier masses of more damp mixture back to the agitator bowl 224 for further agitation and drying.

The particles are drawn downwards along a spiralling column of heated air in cyclone 232 and centrifugal action removes further moisture from the particles. At the bottom of the cyclone 232, the particles are isolated from the air column by airlock 233 and are sorted by a rotary screen 234. Smaller, lighter particles of dried product pass through the rotary screen 234 and exit the dehydrator 220 at outlet 240 for further processing. Larger, heavier particles of damp mixture are redirected to the agitator bowl 224 from outlet 241 for further agitation and drying within several seconds.

With reference again to FIG. 7, heated product 241 exiting the dehydrator 220 from outlet 240. The average transit time through the dryer is between 60 and 90 seconds and the end moisture content below 10% moisture may then be permitted to cool. Some of this dried product 245 may be further used in the co-drying process as a quantity of the dry carrier 211 so as to increase the fluid content of marine constitutents. Temperature sensitive enzyme active products 242 or other bioactive products, which might be denatured by the drying process, may be introduced to the dried product 241 after the product has passed through the dehydrator 220 as illustrated. The dried product 241 then undergoes further mixing and blending at mixing step 250 to ensure the homogenous addition of the temperature sensitive enzyme active products 242. The final product 243 may then proceed to a packaging step such as a bagger 244 or to a storage bin 245 prior to further use in aquaculture or animal feeds.

Concentration and Co-Drying or Krill with Vegetable Proteins Trials

The objectives were the concentration of liquid krill hydrolysate to 42% DM in a rising film plate evaporator. (Alfa Vap). The drying of a krill concentrate blend with soya meal and corn gluten meal in a flash dryer (drier with performance characteristics as defined), to determine the maximum amount of krill concentrate that can be added to the dry vegetable protein meal.

Raw material hydrolysed krill with 18–20% DM including approximately 0.3% oil.

Evaporator. The hydrolysed krill was concentrated in an Alfa Vap evaporator from 18–20% DM to 42% DM. The 42% level was not obtained with any difficulty.

Mixing

The mixing was done in 100 kg batches using a cylindrical container with a vertical shaft paddle. This was accomplished without unusual difficulties.

Drying

Drying and mising was caried out in two steps: Step 1 was mixing the krill concentrate and carrier (vegetable and protein) and drying to about 90% DM. Step 2 was mixing the dried product from step 1 with more krill concentrate and drying a second time.

Flash Drying

The mixtures were dried in a flash dryer. This was done by feeding the mixture into a chamber containing a fast rotating agitator. Through intake air ducts hot air was led through the chamber and agitator.

Impact Temperature was 165–175 deg. C.

Drying Temperature (set point) is 110 deg. C. to 125 deg C.

Capacity

The flow to the dryer for all three test vegetable protein products was 600–700 kg/hr. This gave an evaporation rate of approximately 500 kg/hr. in the dryer.

Results

The temperature of the product is not increased in the dryer by any significatnt ammount. The evaporation of the water on the product keeps the temperature low. The rapid transit of the product through the dryer also minimizes the temperature and time effects that can reduce the value of the product as a feed.

A third or fourth step is also contemplated and considered possible with this type of dryer.

Figure 9:
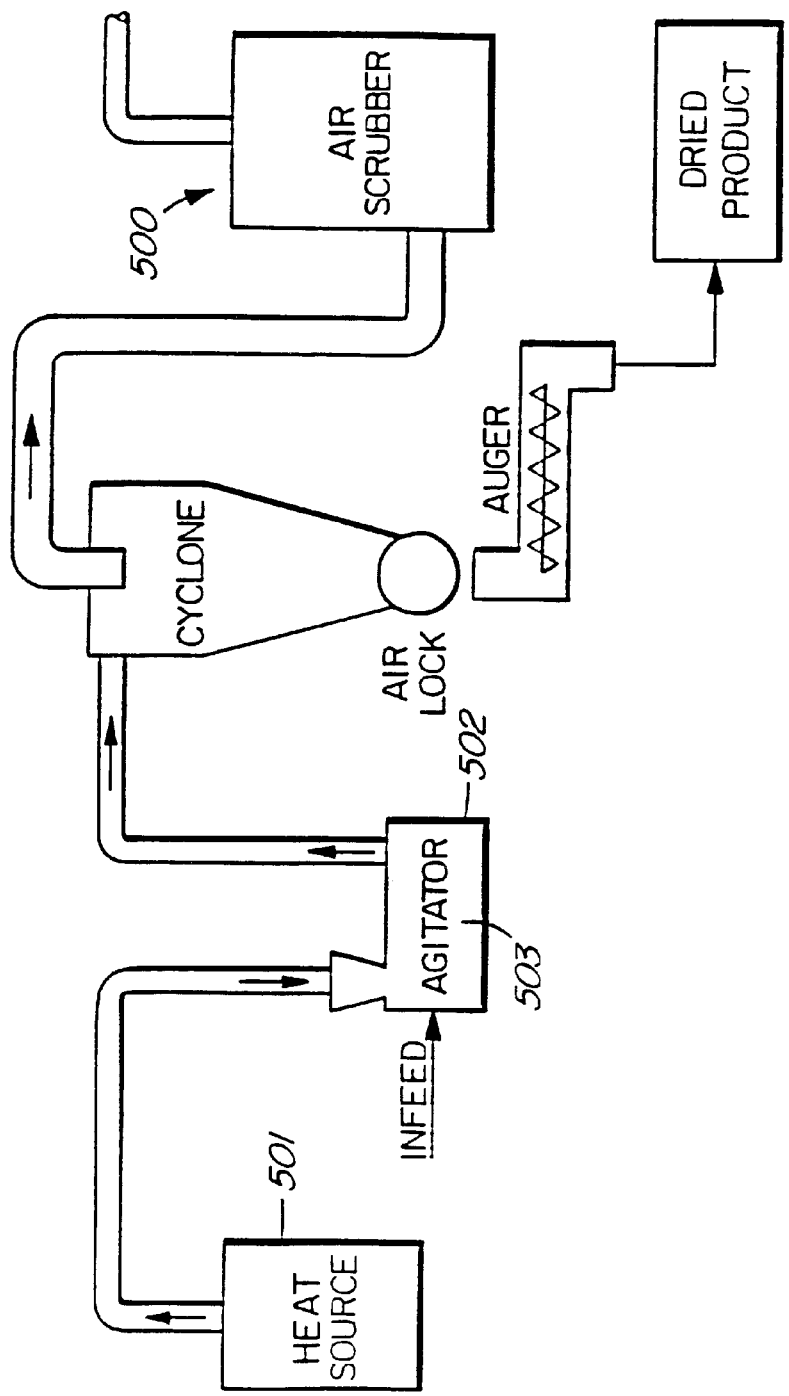
FIG. 9 is a diagrammatic view of the codrying process according to a further aspect of the present invention.

Other driers besides those of ball dryer 81 (FIG. 6) are contemplated. For example, dryers such as direct heated flash driers or fluidized bed driers that cause rapid drying of the particles within a few seconds are well known. With reference to FIG. 9, a built in air scrubber generally illustrated at 500 is used for odor control. A burner or indirect heating system 501 heats the air to the required level with impact temperatures not exceeding 450 deg. C. before the air enters agitator 502, the product is augered tangentially into the agitator chamber 503 where most of the water in the product is evaporated. Agitator 502 rotates with a high tangential speed of the agitator blades concurrent with the tangential air flow. The motion of the agitator 502 causes mechanical fluidization of the particles and comminutes the particles, thus accelerating evaporation. The acceleration of the drying velocity reduces the adverse effect of heat or the heat burden on the product during the drying process.

In yet a further embodiment of the invention, it is contemplated that a process for obtaining enzymes from the *Euphausia superba* species of krill and other krill species is of interest. *Euphasia superba* ("E.s.") is a small crustacean from the Antarctic that contains numerous enzymes that are principally but not exclusively represented by proteases, amylases, chitinases, carboxymethy cellulases, lipases, etc. This enzymatic cocktail as a whole or in a partial purified form can be used for a number of industrial applications such as aquaculture and other general feed manufacturing and the further process of marine and other proteins. The inclusion rate of enzymes in the feed would vary depending on the target species and the composition of the diet. For example, these krill enzyme cocktails can be added to aquaculture diets containing large quantities of vegetable proteins which would otherwise be difficult to process by the animals and which could also be part of specialty diets for larval stages of shrimp and starter diets for salmonids where higher survival rates are required. Krill enzymes may also conveniently be used to produce protein hydrolysates from other proteins to incorporate into diets or to improve the functional properties of these diets. Other potential applications would include the production of flavors, protein and peptide extraction from marine by products, protein and pigment recovery from shrimp and crab shell offal, the production of free amino acids and other benefits relating to the actions of these krill enzymes on biological materials.

Using the processes previously disclosed, it was desired to obtain enzymes from the previously autolysed krill preparations.

Figure 10:
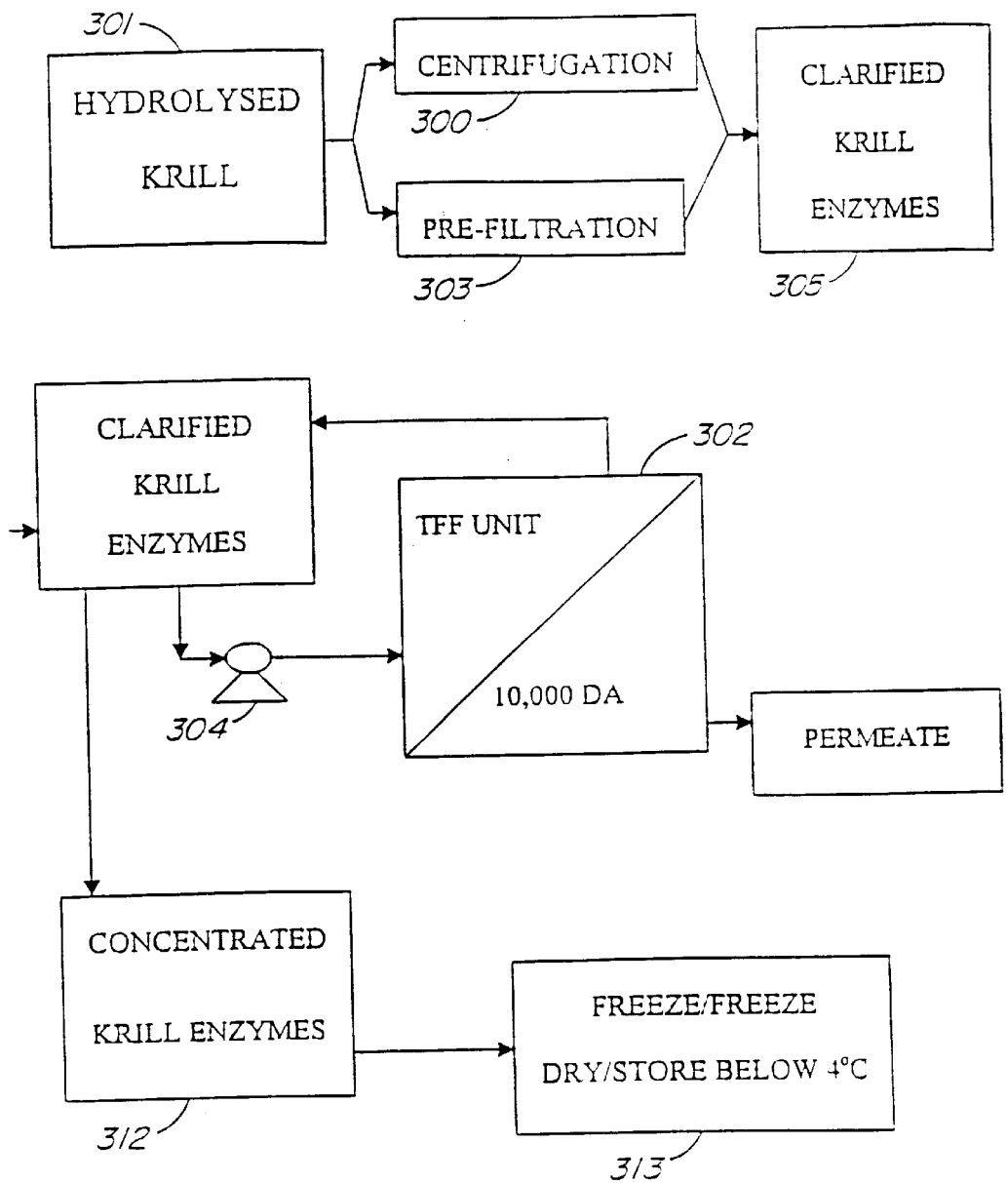
FIG. 10 is a diagrammatic flow chart illustrating the enzyme extraction process utilising hydrolysed krill.

With reference to FIGS. 9 and 10, ultrafiltration membrane 303 was used with the krill hydrolysate 301 and with fresh krill 310. Since most of the krill-derived enzymes have molecular weights above 20,000 daltons, experiments were conducted to determine the most appropriate molecular weight cut-off ultrafiltration membrane to attempt a concentration of the aqueous phase enzyme-rich E.s. and E.p. extracts. It was revealed during experiments that total protease activity begins to become apparent in the filtrates at the 50,000 molecular weight cut off and up. On the other hand, trypsin-like activity is present in filtrates at 30,000 molecular weight cut off. It is therefore desirable to use a 10,000 dalton cut off membrane for filtration purposes.

In order to handle larger volumes of krill hydrolysate and to concentrate the enzyme extracts, a tangential flow filtration ("TFF") cartridge 302 was used using a 10,000 dalton molecular weight cut-off. One such cartridge commercially available is a Millipore Preparative Scale Tangential Flow Filtration cartridge. Such cartridges are intended to handle volumes from 100 ml to 100 liters, although it is readily possible to scale up such techniques to handle larger volumes, if desired. Before subjecting the krill extracts to TFF, they were centrifuged at 4000–10000×G for twenty (20) minutes in a Beckman centrifuge 300 to clarify from solids and eliminate part of the fat. Rather than centrifugation, this clarification step can be replaced by prefiltration 303 with a larger pore filter. After centrifugation, the aqueous phase 305 containing the enzymes of interest was recover and stored at 4 deg. C. The autolysed krill extracts were run through a one square foot TFF cartridge 302 using a Hoechst displacement pump 304. The initial extract volume was about two(2) liters and was brought down to approximately 250–300 ml after four(4) to five(5) hours of operation (below 20 psi of pressure). It was revealed that enzymatic activity recovery differed significantly between the two samples (i.e., autolysed and freshly squeezed extracts).

By measuring the trypsin-like activity ("TLA"), it was found that the recovery of krill enzymes from the fresh frozen krill 310 was relatively smaller than the recovery from hydrolysed krill 301. However, the total units recovered after ultrafiltration were higher for fresh frozen extracts. Accordingly, TLA could be recovered from either freshly squeezed or autolysed krill preparations. Since there was little or no enzymatic activity associated with the filtrate, it is apparent the proteins of interest were not leaching out through the membrane filter.

The resultant enzyme cocktail obtained by the ultrafiltration technique from both the hydrolysed and fresh krill 301, 310, respectively, could then be coupled with freeze drying 313 which would reduce the amount of water associated with the enzymes significantly which would reduce transportation costs. Subsequent processing could then be performed on the enzyme cocktails to further increase the purity and quality of the enzymes present.

Figure 12:
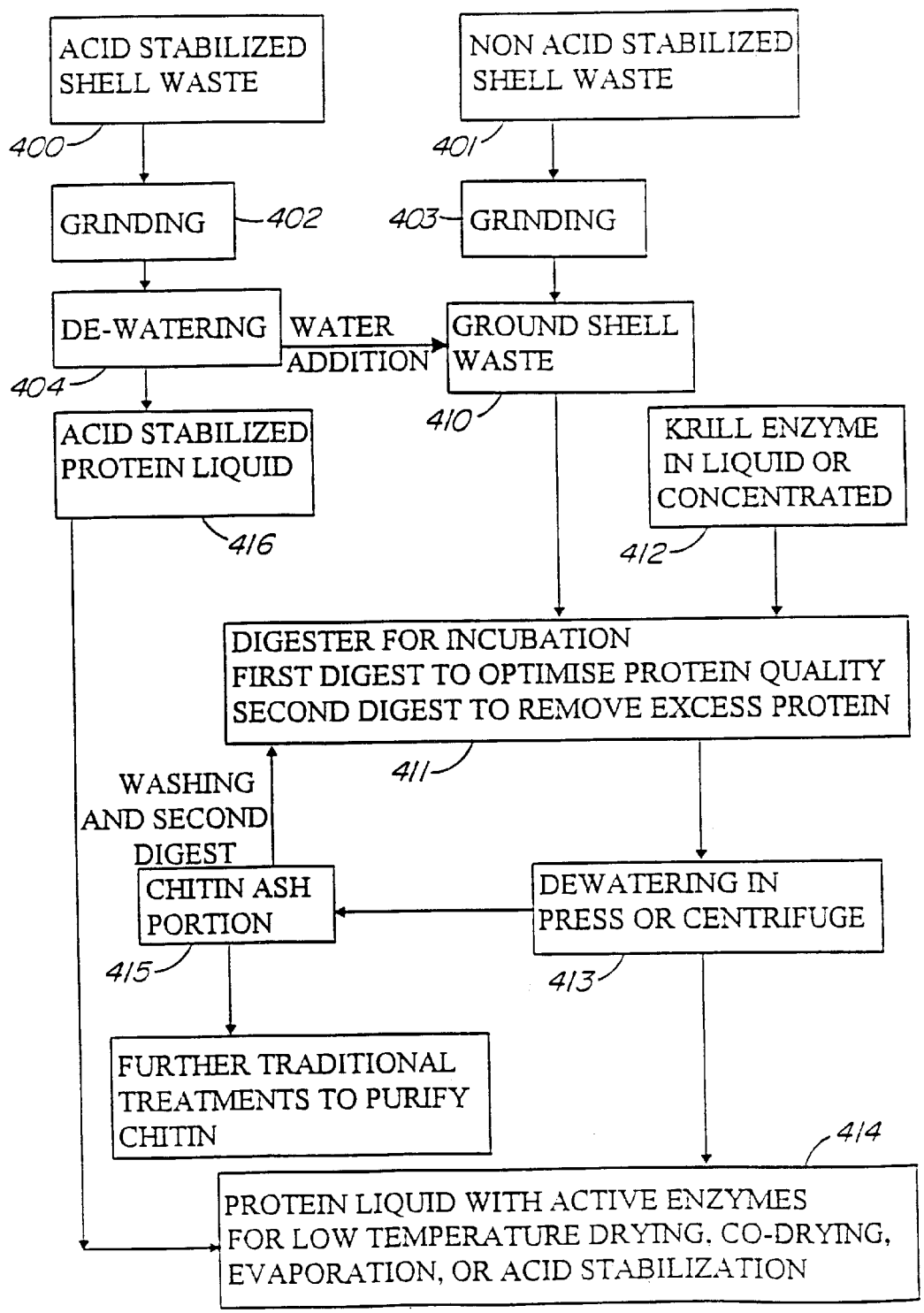
FIG. 12 is a diagrammatic flow chart illustrating the removal of protein and other constitutents from crustacean wastes using krill enzymes according to a further aspect of the present invention.

Yet a further aspect of the invention relates to a method for removal of protein from crustacean wastes using the aforementioned krill enzyme extracts. With reference to FIG. 12, a quantity of crustacean wastes 400, 401 is ground to dried particulate size by grinders 402, 403, respectively, with a portion of water added to facilitate this grinding. Various of a plurality of grinders which will accomplish this include a piranha pump, a macerator or cerator, all of which are known. Acid stabilized shell waste 400 is then de-watered through a de-watering system 404, many of which are readily known to be available, such as the Vincent screw press, wine presses or centrifuges. Non acid stabilized shell waste 401 has no need to be dewatered prior to the addition of enzymes. Water is conveniently added to the de-watered acid stabilized shell waste 410 to facilitate enzymatic reaction. The shell waste 410 is transferred to a digesting tank 411 where an amount of krill enzyme cocktail 412 is added. The enzyme cocktail can be in either a concentrated or non-concentrated form consistent with squeezed extractions from the whole animal as has been described. The squeezed fractions are in the range of 25–75% of the whole animal depending on the amount of enzyme desired and the need to keep the enzyme with the krill to facilitate autolysis. The shell enzyme mixture is subjected to digestion in the digester 411 for a time period in the range of one(1) to forty-eight(48) hrs at a temperature in the range of 0 to 70 Celsius with an optimum temperature being approximately 45 deg. Celsius. Following the digestive process, the mixture is subjected to water removal 413 as has been described. Two fractions will result, a protein rich enzymatically active portion 414 and a shell material portion 415 high in chitin and low in protein. The liquid high protein portion 414 is low temperature dried or co-dried as earlier described or acid stablized. The shell portion 415 can then be further processed by the addition of more enzyme cocktail to facilitate further protein removal in further steps or can be subjected to traditional deproteinization or demineralization techniques as illustrated generally at 420. The extent of de-mineralization necessary can be greatly reduced by the storing of the shell waste for long periods of time while stabilized with acids, preferably formic.

Figure 11:
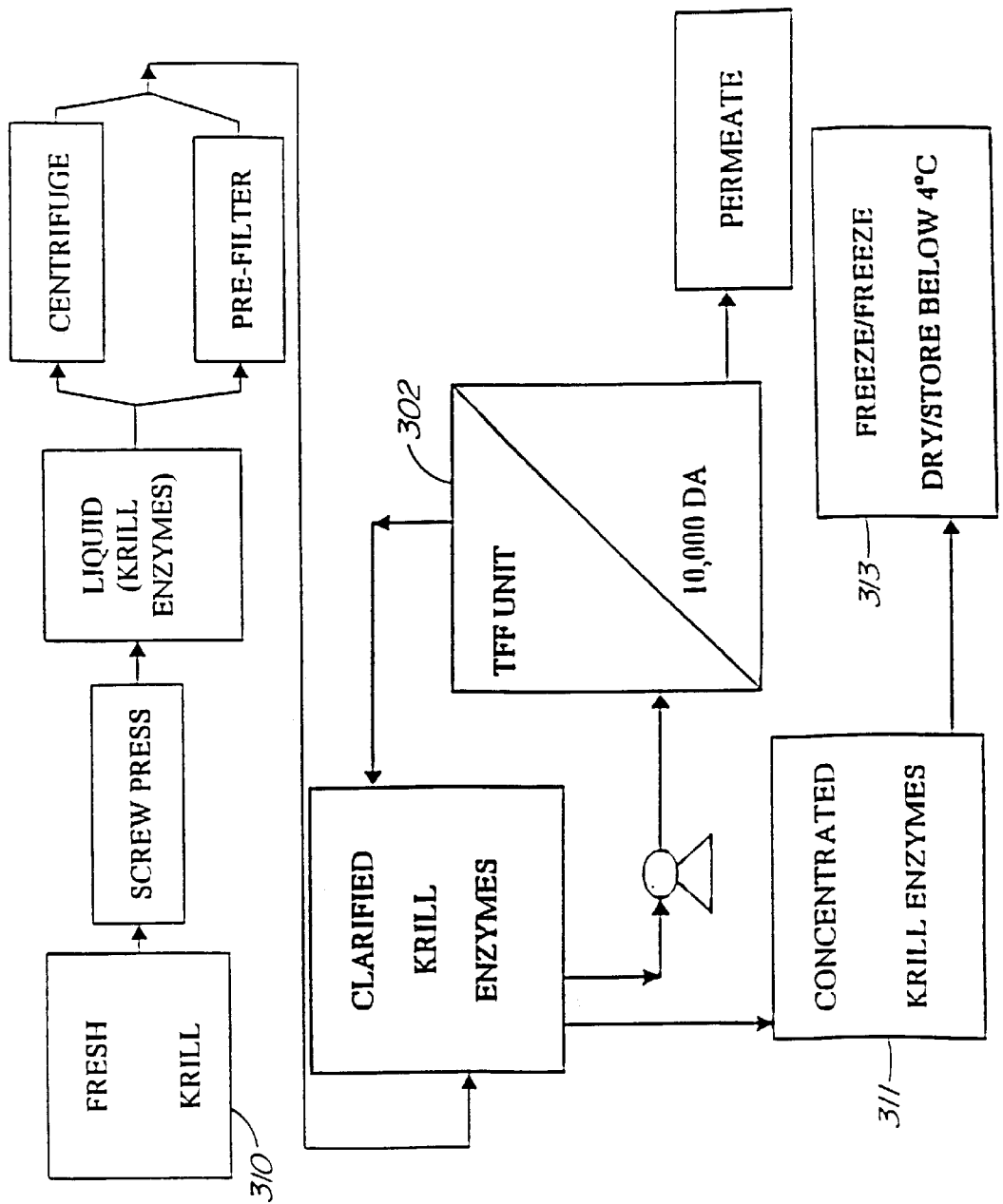
FIG. 11 is a diagrammatic flow chart illustrating the enzyme extraction process utilising fresh krill.

In experiments which have been conducted to date, 70 kg of water was added to 210 kg of mechanically peeled shrimp shell wastes. The slurry was subjected to grinding with a piranha pump to a suitable particle size. 60 kg of this slurry was combined with 15 kg of *Euphasia superba* juice obtained by squeezing whole krill through a screw press 315 (FIG. 11) to obtain 50% by weight of the animal in a liquid form. The shell juice mixture was subjected to digestion for six(6) hours at 45 deg. C. The mixture was dewatered by pressing through a Vincent screw press to obtain the protein rich enzymatically active portion and the shell ash portion 415, as described. The shell portion was approximately 7.5% by weight and the liquid portion made up the remainder. The liquid portion was acid stabilized with 3% by weight formic acid. The shell portion was washed and dried.

In a second trial conducted to establish the efficacy of using krill enzymes for the removal of protein from shrimp shell wastes and the benefit of reincorporating the superba squeezed solids, 26 kg of squeezed superba juice, obtained through the procedures described, was incubated with 10 kg water and 70 kg of ground shrimp shell for six(6) hours at 45 deg C. Samples were taken every hour and squeezed through a screw press. After six(6) hours, 14 kg of squeezed superba solids compising the remainder of the whole animal after enzyme liquid removal were added into the mixture and hydrolyzed for an additional one and one-half (1.5) hours. The remaining slurry was squeezed and the separate fractions were frozen.

While specific embodiments of the invention have been described, such descriptions should be taken as illustrative of the invention only and not as limiting its scope as defined in accordance with the accompanying claims.

We claim:

1. Method of producing a feed product comprising the steps of adding a quantity of concentrated krill hydrolysate to a quantity of liquid marine protein and a quantity of dry carrier to produce a mixture and co-drying said liquid krill hydrolysate and said liquid marine protein with said dry carrier to obtain said feed product while preserving the endogenous enzymes within said hydrolysate.

2. Method as in claim 1 wherein said mixture is mixed prior to co-drying said mixture.

3. Method as in claim 2 wherein said mixture is hydrolyzed by said endogenous enzymes in said liquid krill hydrolysate, said endogenous enzymes remaining within said hydrolysate, prior to said co-drying of said liquid mixture.

4. Method as in claim 3 wherein said mixture is co-dryed in a dryer or other dehydrator.

5. Method as in claim 4 wherein said mixture is ground prior to being subjected to said hydrolysis by said endogenous enzymes.

6. Method as in claim 5 wherein said mixture is cooled following said co-drying of said mixture in said dryer.

7. Method as in claim 6 wherein said dry carrier is one or a combination of dry marine protein meals, dried krill products, dried vegetable matter, and dried fish product.

8. Method as in claim 7 wherein said liquid marine protein is liquid fish product.

9. Method as in claim 8 wherein temperature sensitive enzyme active or other bioactive dry products are added or readded to said mixture following said co-drying of said mixture.

10. Method as in claim 9 and further comprising mixing said temperature sensitive enzyme active products with said mixture.

11. Method as in claim 1 wherein said mixture is co-dryed in a dryer or other dehydrator.

12. Method as in claim 11 wherein said dryer includes an agitator to agitate said mixture entering said dryer.

13. Method as in claim 12 wherein said dryer further includes a drying tower downstream from said agitator and a heat source to provide heat to said tower.

14. Method as in claim 13 and further comprising a classifier downstream of said tower for separating said mixture, said mixture comprising lighter and drier particles and heavier and wetter particles, said classifier separating said lighter and drier from said heavier and wetter particles.

15. Method as in claim 14 wherein said heavier and wetter particles are returned to said agitator.

16. Method as in claim 14 and further comprising a cyclone downstream from said classifier.

17. Method as in claim 16 wherein said cyclone removes further moisture from said heavier particles.

18. Method as in claim 17 wherein said lighter particles are separated into smaller and drier and larger and wetter particles.

19. Method as in claim 18 wherein said larger and wetter particles are returned to said agitator.

20. A feed product produced by the method of any one of claims 1 to 19.

21. Method of producing a concentrated liquid krill hydrolysate comprising the steps of harvesting krill having proteins and other nutrients, digesting said krill through enzymatic activity and partial hydrolysis to obtain liquid krill hydrolysate without deactivating enzymes in said krill, evaporating said krill hydrolysate produced by said enzymatic activity and partial hydrolysis to obtain said concentrated liquid krill hydrolysate and to maintain the nutritional properties of said proteins in said krill.

22. Method of producing a dry krill premix or feedstuff comprising the steps of producing concentrated liquid krill hydrolysate, mixing said concentrated liquid krill hydrolysate and a dry carrier and co-drying said mixture of said concentrated liquid krill hydrolysate and dry carrier.

23. Method of claim 22 wherein said dry carrier is selected from the group of vegetable or animal protein meals and by-products.

24. A feed product as in claim 20 wherein said feed product is an additive.

25. A feed product as in claim 20 wherein said feed product is an ingredient in a compound feed.

26. A product produced by the method of any one of claims 21–23.

27. Method as in claim 5 and further comprising adding liquid to said mixture for assisting said hydrolysis by said endogenous enzymes.

28. Method as in claim 27 wherein said liquid is water.

* * * * *